US00PP10333P

United States Patent [19]

Kelly

[11] Patent Number: Plant 10,333

[45] Date of Patent: Apr. 21, 1998

[54] MINIATURE ROSE PLANT NAMED 'KELDAZ'

[75] Inventor: Martin W. Kelly, High Falls, N.Y.

[73] Assignee: Nor'East Miniature Roses, Inc., Rowley, Mass.

[21] Appl. No.: 824,909

[22] Filed: Mar. 26, 1997

[51] Int. Cl.[6] ..... A01H 5/00

[52] U.S. Cl. ..... Plt./7.1

[58] Field of Search ..... Plt./7.1

*Primary Examiner*—Howard J. Locker

*Attorney, Agent, or Firm*—Christie, Parker & Hale, LLP

[57] ABSTRACT

A new miniature rose with red and white blend flowers.

1 Drawing Sheet

BACKGROUND OF THE INVENTION

The present invention relates to a new and distinct variety of rose plant of the miniature rose class, which was created by crossing as seed parent the variety known as 'Savalife' (U.S. Plant Pat. No. 5,482) and as pollen parent the variety known as 'Benmagic' (U.S. Plant Pat. No. 8,603). The varietal denomination of this new rose is 'Keldaz.'

SUMMARY OF THE INVENTION

Among the novel characteristics possessed by this new variety which distinguishes it from its parents and all other varieties of which I am aware is its attractive red and white blend flowers borne on a plant with abundant dark green foliage.

Asexual reproduction by propagation of vegetative cuttings of the new variety as performed in Essex County, Mass. shows that the foregoing and other distinguishing characteristics come true to form and are established and transmitted through succeeding propagations.

COMPARISON WITH PARENTS

The new variety differs in color from the seed parent and flowers are smaller and different form from pollen parent and with less red coloring on petal.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (RHSCC). The terminology used in color description herein refers to plate numbers in the aforementioned color chart. Phenotypic expression may vary with light availability, environmental and cultural conditions.

Parentage:

*Seed parent.*—'Savalife'.

*Pollen parent.*—'Benmagic'.

Class: Miniature.

The following observations are made of specimens grown under plastic in Essex County, Mass., during June.

Flower

Blooming habit: Continuous.

A. Bud:

(1) *Size.*—Medium.

(2) *Form.*—Oval with acute tip.

(3) *Color.*—As sepals divide, bud color is near 10B with edges and streaks of near 50A.

(4) *Sepals.*—Very slightly bearded; lanceolate; about ⅜-inch longer than the bud color of 3 outermost sepals is near 146B and of 2 innermost sepals is near 146C; sepals stay tight adjacent to outer petals as they open; remain straight out or slightly curved back after petals fall.

(5) *Peduncle.*—Length—about 1⅛ inch. Aspect—slightly curved. Strength—erect. Color—near 146C flushed with near 183C where exposed to sun.

B. Bloom:

(1) *Size.*—Average size when fully expanded up to about 1¾ inches.

(2) *Borne.*—Singly and 2 to a stem.

(3) *Form.*—Opens flat in such a way that top of bloom always appears flat.

(4) *Petalage.*—Number of petals under normal conditions about 20.

(5) *Color.*—Color appears as described for bud until about ½ open when inside of outer petals appear near 45A at outer edges near 9A at base and near 11D in between; reverse is near 10B at base, near 50A on outer edges and near 8A in between; inner petals on top surface are near 9C and near 8A on reverse General tonality from a distance is light red blend.

(6) *Color change.*—As bloom ages, color remains similar with minimal fading to near 9D at center and to near 50D at outer edges; general tonality becomes a yellow and red bicolor and then red coloration lightens after 3 or more days.

C. Petals:

(1) *Texture.*—Thick.

(2) *Appearance.*—Inside and outside satiny.

(3) *Form.*—Broad fan shaped, petal edges reflexing to points.

(4) *Arrangement.*—Imbricated, regularly arranged, shingle-like.

(5) *Petaloids in center.*—1 or 2.

(6) *Persistence.*—Petals Drop.

(7) *Fragrance.*—None.

(8) *Lasting quality.*—Lasting well on plant.

Reproductive organs

A. Stamens, filaments and anthers:

*Arrangement.*—Regularly arranged around style.

B. Stamens:
*Quantity.*—Average.
C. Filaments:
*Approximate length.*—Uneven in length, up to about 5/16 inch.
*General color.*—Near 2C at base, then near 12B.
D. Anthers:
*Color.*—Near 15D.
E. Pollen:
*Color.*—Near 16A.
*Quantity.*—Small amount.
F. Pistils:
*Quantity.*—Fewer than 20.
G. Styles: Usually even, about 7/32 inches, bunch at center of receptacle.
*Color.*—Near 138C.
H. Stigmas:
*Color.*—Near 139D.
I. Hips:
*Shape.*—Globular.
*Size.*—About 3/8 inch diameter.
*Seeds.*—Seeds do not protrude.
*Color.*—Brownish-red.

Plant

A. Form: Upright and compact.
B. Growth: Vigorous, uniform branching.
*Height.*—About 15 to 18 inches.
*Length of flowering stem: About* 4½ inches to 6½ inches. C. Foliage: Compound of 5–7 leaflets, occasionally 3.
*Size.*—Medium.
*Quantity.*—Abundant.
*Color.*—New foliage: Upper side near 147A and near 146B along veins with edges near 183A; underside near 146C flushed with near 183B. Old foliage: Upper side near 147A; under side near 147C flushed with near 183C.
*Shape.*—Oval, pointed.
*Texture.*—Upper side semi-glossy when young, matte when mature; underside matte.
*Thorns or prickles.*—About 1 to 4 on underside of leaf stem.
*Edge.*—Serrated.
*Serration.*—Uneven.
*Leaf stem.*—Between near 147B and 137C with underside near 144A
*Stipules.* Finely bearded.
*Resistance to Diseases.*—Blackspot: Very good. Mildew: Very good. Rust: Very good.
D. Wood:
*New wood.*—Color 147C flushed with near 181A; near 181A in sun; bark smooth.
*Old wood.*—Color between near 147B and near 137C; bark smooth.
Thorns:
*Quantity.*—Ordinary on main stalk; many on laterals, vary in length.
*Form:* Straight, sometimes angel down.
*Length.*—Variable and more so toward ends of laterals.
*Color.*—Near 183D.
*Position.*—Irregular becoming closer together toward ends of laterals.
F. Prickles:
*Main stalk.*—None.
*Laterals.*—Few-to-many at ends of laterals.
*Leaves.*—About 1 to 4prickles on underside at leaf stems.
G. Winter hardiness: Needs protection in severe climate.

I claim:

1. A new and distinct variety of rose plant of the miniature rose class, substantially as shown and described.

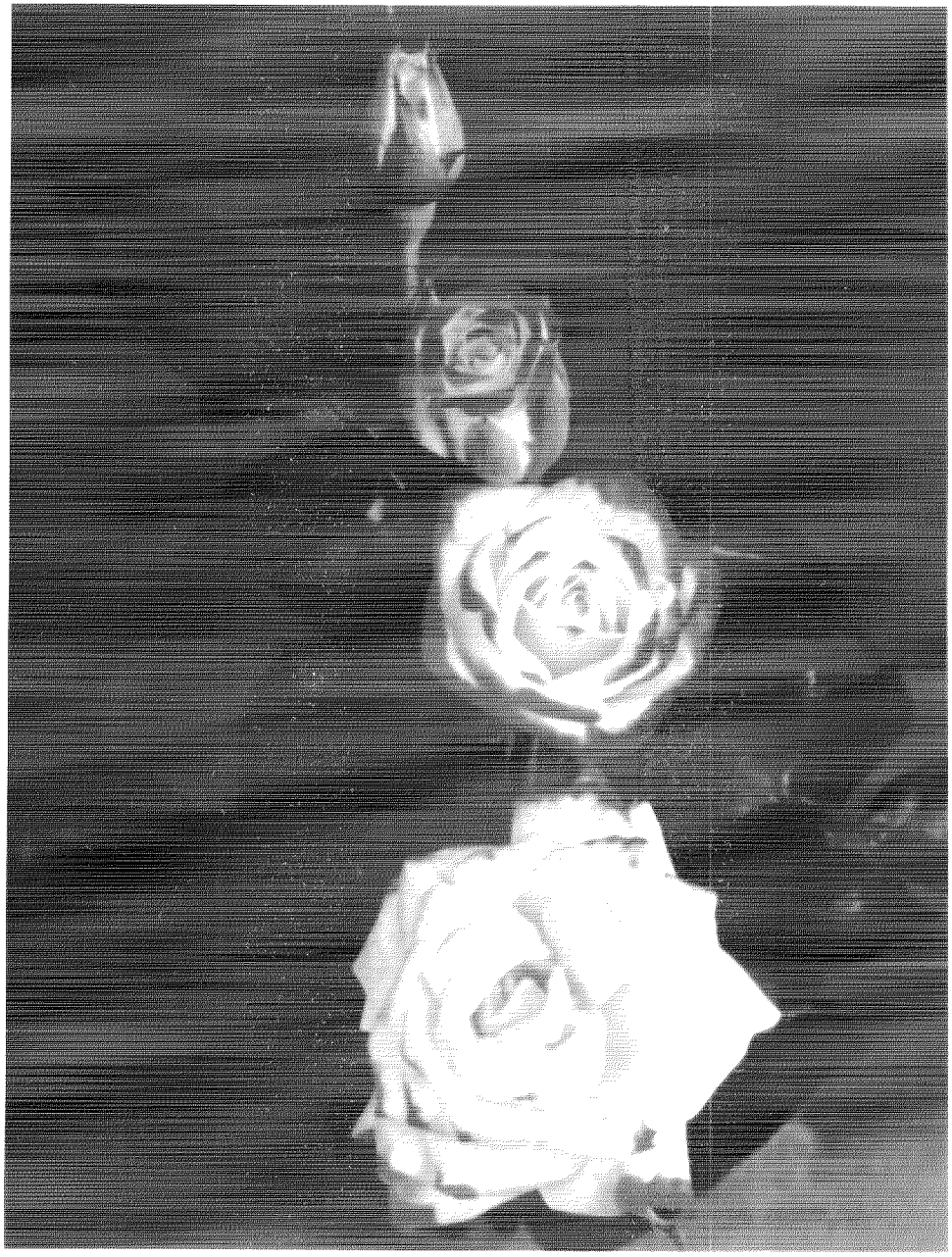

* * * * *